United States Patent [19]

Larsson

[11] Patent Number: 4,687,466

[45] Date of Patent: Aug. 18, 1987

[54] BREASTFEEDING ASSISTANCE DEVICE

[75] Inventor: Karl O. A. H. Larsson, Zug, Switzerland

[73] Assignee: ISG AG, Zug, Switzerland

[21] Appl. No.: 805,441

[22] Filed: Dec. 5, 1985

[51] Int. Cl.[4] .............................................. A61M 37/00

[52] U.S. Cl. .................................... 604/82; 215/11 B; 215/11 D

[58] Field of Search ............... 604/82, 405; 215/11 R, 215/11 B, 11 D; 248/102-104

[56] References Cited

U.S. PATENT DOCUMENTS

| | | | |
|---|---|---|---|
| 147,909 | 2/1874 | Curtiss . | |
| 279,935 | 4/1893 | Smith et al. . | |
| 682,464 | 9/1901 | Graham-Yooll | 215/11 D |
| 696,328 | 3/1902 | Graham-Yooll | 215/11 D |
| 2,313,219 | 3/1943 | Bulling | 604/405 |
| 2,328,569 | 9/1943 | McGaw . | |
| 2,372,281 | 3/1945 | Jordan | 215/11 B |
| 2,697,531 | 12/1954 | Hood . | |
| 2,708,421 | 5/1955 | Jauch . | |
| 2,756,740 | 7/1956 | Deane . | |
| 2,760,664 | 8/1956 | D'Amico et al. . | |
| 2,775,240 | 12/1956 | Morrisey, Jr. et al. | 604/405 |
| 2,853,069 | 9/1958 | Beacham et al. . | |
| 2,883,985 | 4/1959 | Evans . | |
| 2,923,296 | 2/1960 | Adams et al. . | |
| 2,969,064 | 1/1961 | Metz . | |
| 3,086,525 | 4/1963 | Whitcomb . | |
| 3,263,848 | 8/1966 | Zackheim . | |
| 3,426,755 | 2/1969 | Clegg . | |
| 3,757,784 | 9/1973 | Avery . | |
| 3,977,638 | 8/1976 | Woodard | 248/102 |
| 3,990,597 | 11/1976 | Barton . | |

FOREIGN PATENT DOCUMENTS 7673 of 1886 United Kingdom ............. 215/11 D

*Primary Examiner*—C. Fred Rosenbaum
*Assistant Examiner*—Gene B. Kartchner
*Attorney, Agent, or Firm*—Willian Brinks Olds Hofer Gilson & Lione Ltd.

[57] ABSTRACT

A device is disclosed for providing a suckling infant with a liquid diet supplement simultaneously with normal breast feeding. Improvement in suckling in the child and stimulation of the mother's milk supply are thereby encouraged. The device includes a container for holding the supplement and at least one tube communication with the supplement having an end which is positioned adjacent the user's breast nipple. A valve mechanism seats on the container mouth, and is comprised of a valve mount on which a flexible valve member is received. A portion of the valve member covers an aperture formed in the valve mount. The valve member prevents liquid from escaping through the aperture, but allows air to enter the container through the aperture when liquid is removed by suckling. The valve mechanism also permits ready and thorough cleaning of the thin tubing used. A cleaning solution placed in the container can be forced through the tubing by squeezing the container, with the valve member preventing the solution from flowing out the aperture. Two tubes are preferably carried by the valve member and extend through slots formed in the valve mount. Several interchangeable valve members are provided which each have a different diameter tubing for adjustment of fluid flow. A neck cord for suspending the device in position on the chest is also disclosed, along with an attachment ring for the valve mechanism which has a plurality of notches into which the tubing can be wedged to pinch it cloes when not in use.

12 Claims, 5 Drawing Figures

FIG. 1
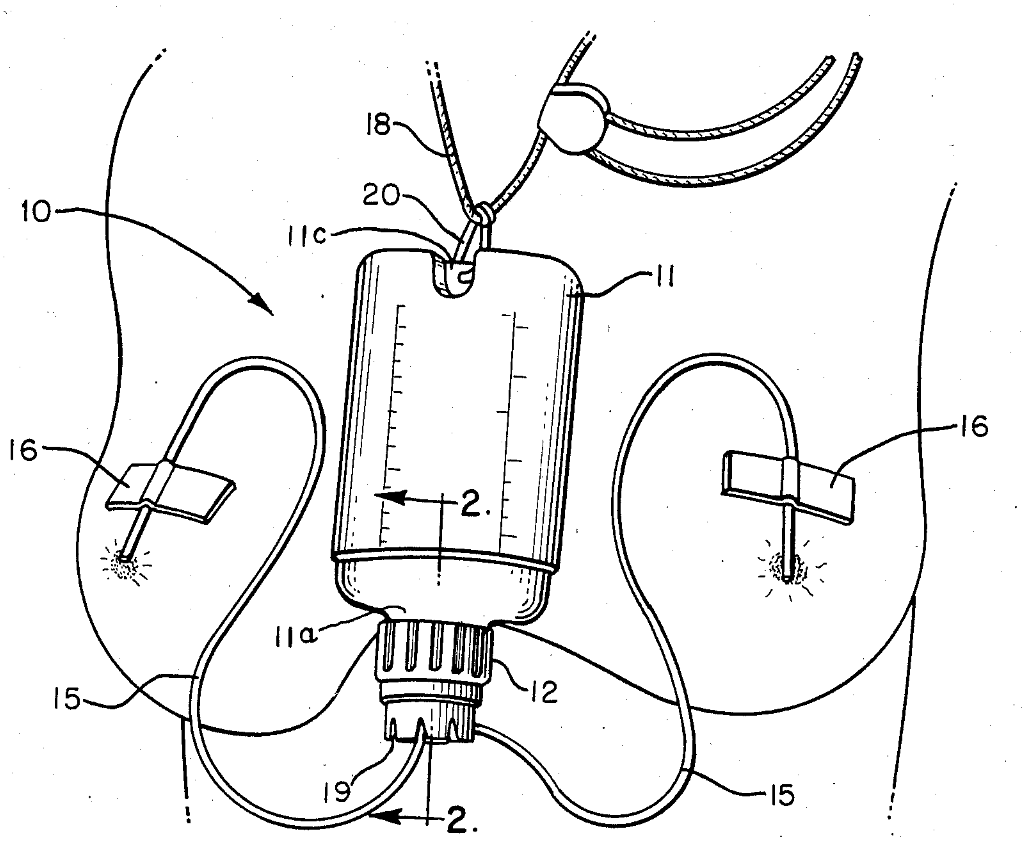
FIG. 4
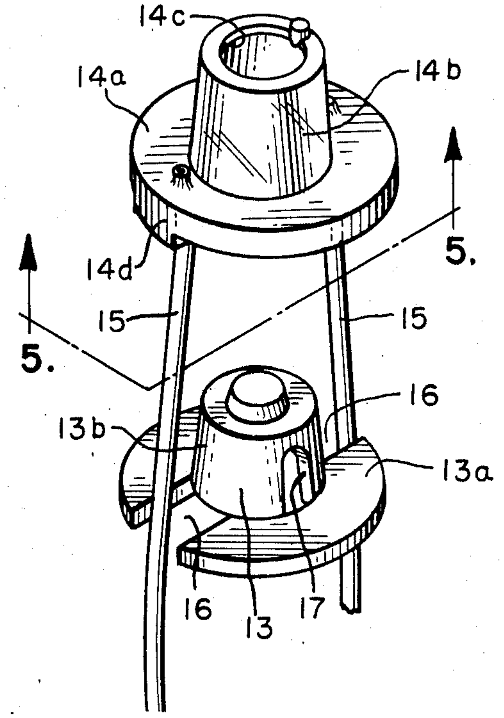
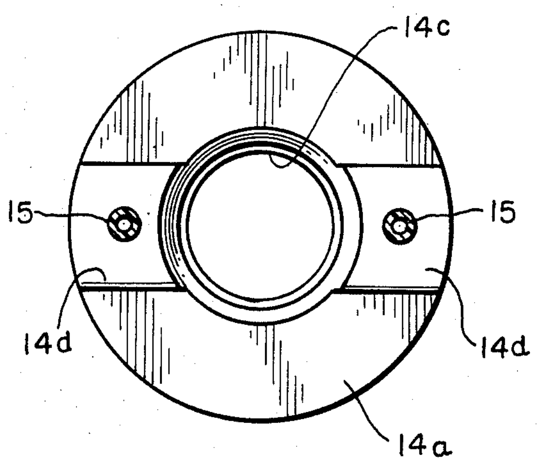
FIG. 5

BREASTFEEDING ASSISTANCE DEVICE

FIELD OF THE INVENTION

This invention relates to devices for providing a diet supplement to a suckling child simultaneously with normal breastfeeding, that is feeding at the breast.

BACKGROUND OF THE INVENTION

There are many instances where the amount of milk which a suckling infant is receiving from the breast needs to be augmented. For instance, some babies have difficulty learning to suckle the breast. This can lead to a reluctance to breast feed, since the infant does not receive immediate gratification upon suckling. The mother's milk supply may often be inadequate, such as from a temporary reduction in milk supply from mother-baby separation, illness or the like.

It is also possible for an adoptive mother to induce lactation. The mammary glands can be stimulated to begin to produce milk. The induction of lactation can take some time, however. Moreover, most women will not be able to exclusively breastfeed the adopted child.

While the milk supply can be supplemented in these instances with bottle feeding, it is most desirable to be able to provide the diet supplementation simultaneously with normal breast feeding. This serves to stimulate the production of more milk, improves suckling where necessary, and further perpetuates the mother-child bonding incident with breastfeeding.

There are a number of considerations in designing a device to so supplement the milk supply during breastfeeding. First, it should deliver the supplement to the infant in an unobtrusive manner. The user should also be comfortable with the device, and be able to use it with relative ease.

The child must also be able to get the breast nipple and the supplement delivery means into its mouth simultaneously. A small diameter delivery tube can be used to this end. Such a tube can be difficult to clean after use, however.

SUMMARY OF THE INVENTION

It is a principal objective of the present invention to provide a breast feeding assistance device which is easily used to supplement the user's milk supply simultaneously with normal nursing, which is comfortable for the user, and which can be readily cleaned after use.

This objective has been realized in the present invention, which comprises a container for holding the liquid supplement, and a fluid delivery mechanism carried on the container which includes an air valve for the container.

The container has a neck portion terminating in a lip, and in its preferred form is a rigid plastic bottle. The fluid delivery mechanism is attached to the container lip to close the container mouth. At least one small diameter elongated flexible tube extends into the container through the delivery mechanism, and has its other end located adjacent a breast nipple. The tubing is sized so that it easily fits in the infant's mouth along with the breast nipple. Two tubes, one for each breast, are advantageously provided in a present embodiment enabling the infant to be readily switched from one breast to the other.

The air valve is comprised of a valve mount on which is received a flexible valve member. A portion of the valve member covers an aperture in the valve mount, and thereby forms a flap-type valve. This valve is mounted in the container opening with the flexible valve member inboard relative to the container (i.e., within the container). The container is otherwise closed, with the exception of the tubing which extends into the supplement.

Air passes into the container through the valve to relieve any negative pressure build-up (vacuum) caused by removal of supplement through suckling, while fluid is prevented from escaping back through the aperture. A fairly snug fit between the flexible valve member and the valve mount is maintained to assure that a degree of suckling effort is required of the infant in order to receive the supplement.

Use of this fluid delivery mechanism facilitates cleaning of the device, and of the tubing in particular. Cleaning fluid, such as soapy water, is first placed in the container and the valve and tubing is then attached. Squeezing the sides of the container then forces the cleaning fluid through the thin tubing, since the valve remains closed. A rinse solution can then be applied in the same manner. The tubing is thus readily cleaned.

A present embodiment of the invention provides a plurality of interchangeable valve members which each have tubing with a different internal diameter. In this regard, the tubing is also advantageously made integral with the valve member. The rate of flow of supplement can thereby be controlled through the selection of a valve member with the appropriate size tubing.

This present embodiment also provides an adjustable neck cord which is used to suspend the container on the user's chest. The container is preferable located with the fluid delivery mechanism at about the same level as the breast nipples or slightly below. The position serves to substantially eliminate gravity feed, assuring that the supplement is withdrawn by suckling alone.

This embodiment also includes a plurality of small notches which are formed on a part of the device, such as on an extended collar of a retaining ring used to attach the valve unit to the container lip. The notches are sized so that tubing can be wedged therein and pinched closed when not in use.

The foregoing features and advantages of the present invention will be more readily understood upon consideration of the following detailed description which, taken in conjunction with the accompanying drawings, discloses a presently preferred embodiment of the invention.

BRIEF DESCRIPTION OF THE DRAWINGS

FIG. 1 is an elevational view of a device made in accordance with the present invention positioned on a user's chest;

FIG. 4 is an enlarged exploded perspective view of the valve member and valve mount, including tubing; and FIG. 5 is a sectional view taken along line 5—5 of FIG. 4.

DETAILED DESCRIPTION OF A PRESENTLY PREFERRED EMBODIMENT OF THE INVENTION

Figure 2:
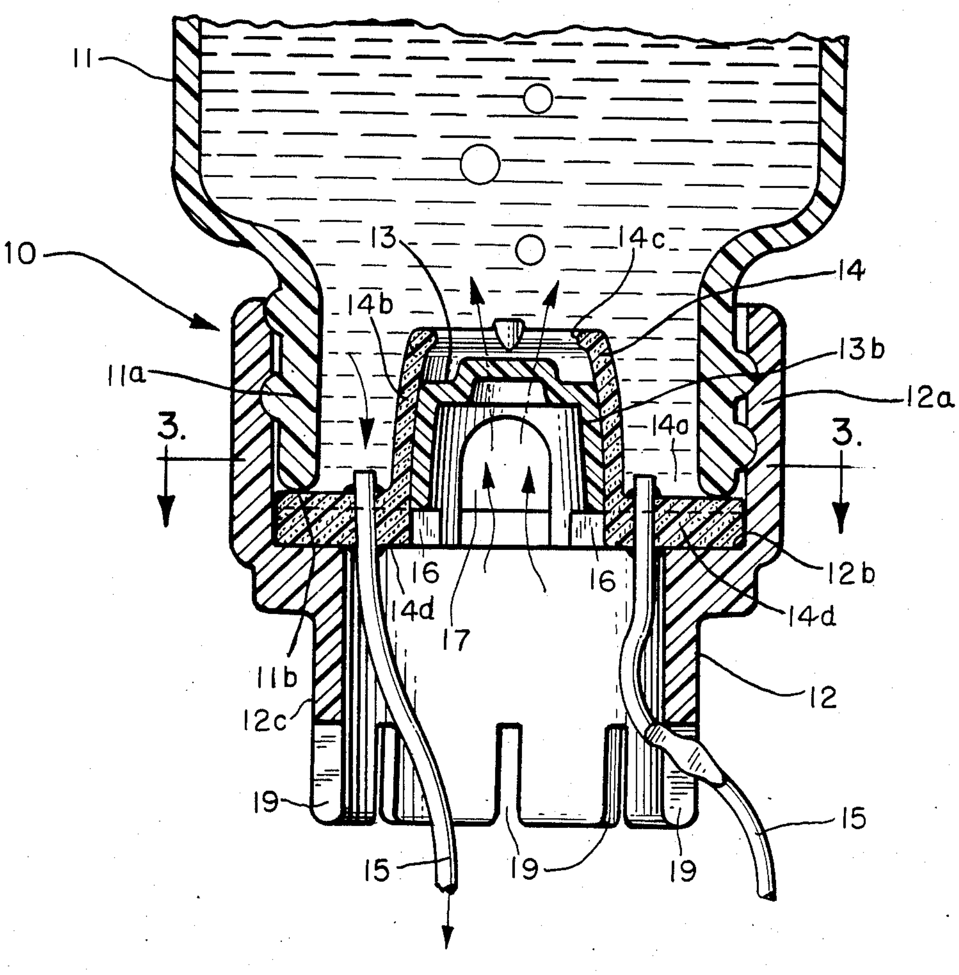
FIG. 2 is an enlarged sectional view taken along line 2—2 of FIG. 1.

Referring to FIGS. 1 and 2, the supplemental nursing device 10 has a container 11 in the form of a rigid transparent plastic bottle having a neck portion 11*a* terminating in a lip 11*b*. The container 11 is otherwise closed except for the opening defined by the lip 11*b*. Gradations can be provided on the container exterior to assist in measuring liquid supplement.

A fluid delivery mechanism is attached to the lip 11*b* by an attachment ring 12. The fluid delivery mechanism includes a valve mount 13 on which is received one of a plurality of interchangeable flexible valve members 14. Each of the valve members (only one of which is shown) has a pair of elongated flexible tubes 15 extending therethrough.

The tubes 15 are made of a transparent silicone rubber. One end of each tube 15 is fixed with a silicone glue within a respective throughbore formed in the flexible valve member 14, which is also made of a transparent silicone rubber. The other end of each tube 15 is located adjacent a breast nipple (FIG. 2). A piece of medical adhesive tape 16 is advantageously used to position this free end of the tubing. It will be noted that a sufficient length of tubing 15 is provided to allow the tubing to be looped and place directly on the breast. Supplement is thereby warmed by body-heat as it passes through the tubing 15.

The tubing 15 is of a small size, and its free end readily fits within the infant's mouth along with the breast nipple. The tubing 15 is also provided in different internal diameters for each of the valve members 14. For instance, a present embodiment has three valve members which respectively have tubes 15 with internal diameters of 0.65 mm, 0.75 mm and 0.85 mm. The interchangeability of the flexible valve members 14 allows the user to easily adjust the rate of supplement flow by the selection of a valve member 14 having the appropriate tube size.

The valve formed by the valve mount 13 and a flexible valve member 14 allows air to enter the container 11 in response to the removal of supplement through suckling, but prevents supplement from otherwise escaping form the container. As will be noted in FIG. 1, the container 11 is used in an "inverted" configuration, i.e. the container opening is downward. The valve extends inboard (into) the container, and is thus immersed in the supplement in use.

It will be noted that the terms "inboard" and "outboard" used herein are with reference to the assembled device.

With particular reference to FIGS. 2 and 4, the valve mount 13 has a disk shaped base portion 13*a* which has a pair of radially extending slots 16 formed therein. A hollow boss 13*b* extends from the inboard side of the base 13*a*, and has an aperture 17 formed in its sidewall. The valve mount 13 is made of a rigid plastic material.

Each valve member 14 also has a disk shaped base portion 14*a* which overlies and covers the surface of the valve mount base 13*a*. A sleeve portion 14*b* extends from the inboard side of the base 14*a*. The sleeve portion 14*b* has an axial (vertical) height which is slightly greater than that of the boss 13*b*, and terminates in an opening surrounded by a bead 14*c*.

The flexible valve member 14 fits on the valve mount 13 with the two bases 13*a*,14*a* in facial engagement and the sleeve 14*b* over the boss 13*b*. Two block portions 14*d* (FIGS. 4 and 5) depend from the outboard side of the base 14*a*. These block portions are received in the slots 16 of the valve mount base 13*a*, and serve to position the tubes 15 in the slots. The sleeve 14*b* has a radial diameter which is slightly smaller than that of the boss 13*b*, so that the sleeve 14*b* is stretched over the boss 13*b* in a snug fit. The aperture 17 is covered in this manner.

The attachment ring 12 is used to seat the fluid delivery mechanism on the lip 11*b* of the container 11 (FIG. 2). Both of the bases 13*a*,14*a* are approximately the same diameter as the container lip 11*b* to this end. The attachment ring has a portion 12*a* which is internally threaded and is received on the threaded container neck 11*a*. An internal shoulder 12*b* is formed at the outboard end of the threaded portion 12*a*, and a collar 12*c* extends outboard from this shoulder.

The fluid delivery mechanism is inserted into the attachment ring 12 (tubes 15 first) so that the outboard side of the valve mount disk 13*a* abuts the internal shoulder 12*b*, the latter having an interior diameter smaller than that of the base 13*a*. The attachment ring 12 is then screwed onto the container neck 11*a* until the inboard side of the valve member base 14*a* abuts the container lip 11*b*. This closes the container opening (except for the tubing 15 which communicates with the container interior).

The flexible base 14*a* of the valve member 14 thus further serves as a sealing gasket between the lip 11*b* and the valve mount base 13*a*. It will be noted in this regard that the valve member blocks 14*d* have approximately the same axial thickness as the valve mount base 13*a*. A bearing surface for the shoulder 12*b* is thereby provided around the entire outboard edge of the valve 13,14 to effect a good seal.

Figure 3:
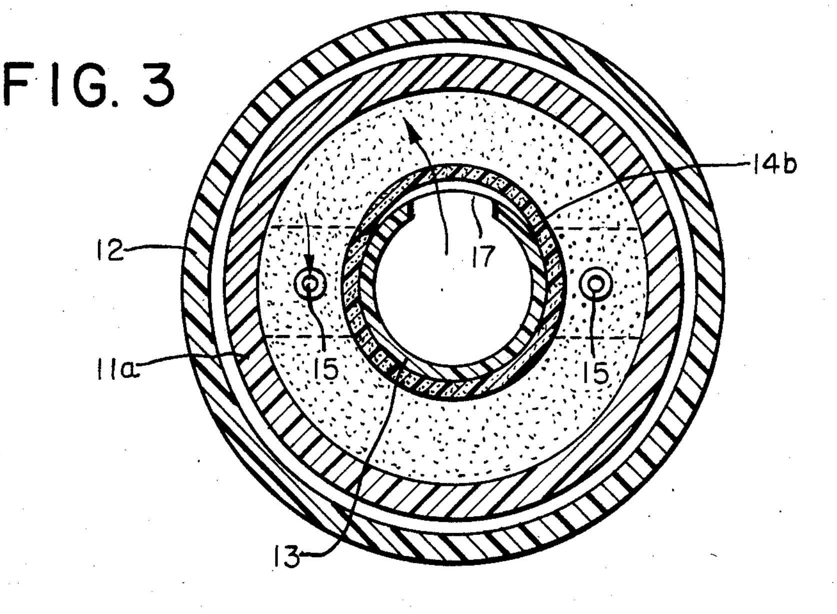
FIG. 3 is a sectional view taken along line 3—3 of FIG. 2.

In use, the valve 13,14 allows air to enter the container in response to the removal of supplement caused by suckling. That is, a negative pressure in the container develops during suckling which is relieved when the ambient air pressure causes the flexible sleeve portion 14*b* to be distended inboard, which then allows an air bubble to pass through the aperture 17 and out the opening of the sleeve portion 14*b* into the container. (This distention of the sleeve portion 14*b* is illustrated by the slight bulge in the sleeve portion adjacent the aperture 17 in FIG. 3.) The aperture 17 is quickly closed by the sleeve portion 14*b* returning into place after an air bubble passes. This prevents supplement from escaping through the aperture 17.

This fluid delivery mechanism also facilitates cleaning of the thin tubing 15 after use. Cleaning solution placed in the container 11 can be forced through the tubing 15 by squeezing on the sides of the container 11 (with the device assembled). A rinse solution can then be passed through the tubing 15 in a like manner.

The collar portion 12*c* of the attachment ring 12 has a plurality of notches 19 formed thereon. These notches 19 are sized so that the flexible tubing 15 can be wedged therein and thereby pinched closed (FIG. 2) when not in use. For example, the tube 15 going to the breast which is not currently being suckled would be pinched off in this manner. It will of course be recognized that the notches 19 could be formed on another part of the device, as desired.

An adjustable neck cord 18 is also advantageously provided (FIG. 1) to suspend the device 10 in place on the user's chest. The neck cord 18 has a snap-lock hook 20 which is attachable to a loop 11*c* formed on the "bottom" of the container 11. The preferred location for the device is with the fluid delivery mechanism, i.e. the container opening, at or a little below about the level of the breast nipples. This serves to reduce any gravity feed which might occur if the device was located higher, and assures that only suckling will draw supplement from the container 11.

The preferred application of the invention is in the aforementioned inverted condition with the valve 13,14 immersed in the supplement. It should be recognized that the device could be adapted to be used in an "upright" configuration as well.

The breast feeding assistance device of this invention can be provided to the user in the form of a kit. The kit contains the elements described above and additionally includes one or more rolls of medical adhesive tape (for securing the tubes 15 in position), and a snap-fit cap for the device which is useful when traveling.

Thus, while the invention has been described in connection with a certain presently preferred embodiment, those skilled in the art will recognize many modifications of structure, arrangement, portions, elements, materials, and components which can be used in the practice of the invention without departing from the principles of the invention.

What is claimed is:

1. A device for delivering a liquid diet supplement to a nursing infant simultaneously with normal breastfeeding, comprising:

a non-collapsible container for holding the liquid supplement, said container having a neck portion defining a container opening which is downwardly directed during breastfeeding, said container being otherwise closed;

a fluid delivery mechanism comprising a valve mount having a first aperture formed therein through which the interior of said container is accessed for liquid supplement outflow, and a second aperture formed therethrough, and a plurality of flexible valve members being interchangeably received on said valve mount to cover said second aperture, each said valve member being biased to close said second aperture and adapted to substantially prevent liquid supplement from flowing out of said container through said second aperture while permitting air to enter said container in response to a negative pressure within said container sufficient to overcome said valve member bias caused by liquid supplement outflow from suckling, said bias being related to a desired level of suckling effort, each said valve member carrying tubing having a first end communicating through said opening via said first aperture with said liquid supplement in said container interior, and a second end which is positioned adjacent a breast nipple for suckling, said second end being sized to fit into the infant's mouth simultaneously with the breast nipple, said tubing of each said valve member providing a rate of delivery for a given suckling effort that is different from the rate of another valve member, said plurality of valve members thereby permitting control of liquid supplement delivery by selection of a valve member with the appropriate delivery rate; and means for removably attaching said fluid delivery mechanism to said neck portion and sealing said opening.

2. A device for delivering a liquid diet supplement to a nursing infant simultaneously with normal breastfeeding, comprising:

a non-collapsible container for holding the liquid supplement, said container having a neck portion defining a container opening which is downwardly directed during breastfeeding, said container being otherwise closed;

a fluid delivery mechanism comprising a valve mount having a first aperture formed therein through which the interior of said container is accessed for liquid supplement outflow, and a second aperture formed therethrough, said valve mount further including a rigid diskshaped base having an inboard side facing said container interior and an outboard side, a raised boss extending from the inboard side of said valve mount base, said boss having said second aperture formed therein, at least one gap comprising said first aperture formed in said valve mount base through which said tubing passes, a flexible valve member received on said valve mount and covering said second aperture, said valve member comprising a flexible disk-shaped base which overlies and covers the inboard side of said valve mount base, and a flexible sleeve portion which fits over and surrounds said boss to cover said second aperture, said sleeve portion being open at its inboard end and sized slightly smaller in diameter than said boss to form a snug fit therewith, said valve member being biased to close said second aperture and adapted to substantially prevent liquid supplement from flowing out of said container through said second aperture while permitting air to enter said container in response to a negative pressure within said container sufficient to overcome said valve member bias caused by liquid supplement outflow from suckling, said bias being related to a desired level of suckling effort, at least one elongated tube carried by said mechanism having a first end communicating through said opening via said first aperture with said liquid supplement in said container interior, and a second end which is positioned adjacent a breast nipple for suckling, said second end being sized to fit into the infant's mouth simultaneously with the breast nipple; and means for removably attaching said fluid delivery mechanism to said neck portion and sealing said opening.

3. The breastfeeding assistance device of claim 2 wherein said valve member has said tubing formed integral therewith.

4. The breastfeeding assistance device of claim 3 wherein said fluid delivery mechanism further comprises a plurality of valve members each having tubing with a different second end interior tube diameter, said plurality of valve members being interchangeable on said valve mount to thereby permit control of liquid supplement delivery by selection of a valve member with the appropriate diameter tubing.

5. The breastfeeding assistance device of claim 2 wherein said valve mount base has two gaps therethrough in the form of radially extending slots having a small axial depth, said valve member having two block portions which are received in respective slots, a tube being mounted in each block portion, said block portions having an axial thickness about equal to the depth of said slots such that the outboard side of said valve mount base and said block portion surfaces are flush, said means for removeably attaching said fluid delivery mechanism comprising a ring which is threaded to said neck portion, said ring having an interior shoulder on which said outboard side of said valve mount seats, said flexible base of said valve member forming a sealing gasket between said valve mount and a lip on said neck portion defining said container opening.

6. The breastfeeding assistance device of claim 5 wherein said ring includes an outwardly extending collar, said collar having a plurality of notches formed therein within which said tubing can be wedged and pinched shut when not in use.

7. A device for delivering a liquid diet supplement to a nursing infant simultaneously with normal breastfeeding, comprising:

a non-collapsible container for holding the liquid supplement, said container having a neck portion defining a container opening, said container being otherwise closed, a valve mount having a first aperture formed therein through which the interior of said container is accessed for liquid supplement outflow, and a second aperture formed therethrough, and a plurality of flexible valve members interchangeably received on said valve mount to cover said second aperture, each said valve member being biased to close said second aperture and adapted to substantially seal off said second aperture while permitting air to enter said container in response to a negative pressure within said container sufficient to overcome said valve member bias caused by liquid supplement outflow from suckling, said bias being related to a desired level of suckling effort, at least one elongated tube carried by each of said valve members, each said tube having a first end communicating with said liquid supplement in said container interior through said opening via said first aperture, and a second end which is positioned adjacent a breast nipple for suckling, said second end being sized to fit into the infant's mouth simultaneously with the breast nipple, each valve member having tubing with a different second end interior tube diameter, thereby permitting control of liquid supplement delivery by selection of a valve member with the appropriate diameter tubing; and means for removably attaching said valve to said neck portion and sealing said opening.

8. The breastfeeding assistance device of claim 7 wherein two tubes are employed, one for each breast nipple, said valve mount comprising a rigid disk-shaped base having an inboard side facing said container interior and an outboard side, a raised boss extending from the inboard side of said valve mount base, said boss having said second aperture formed therein, two gaps comprising said first aperture formed in said valve mount base through which a respective tube passes, each said valve member comprising a flexible disk-shaped base which overlies and covers the inboard side of said valve mount base, and a flexible sleeve portion which fits over and surrounds said boss to cover said aperture, said sleeve portion being open at its inboard end and sized slightly smaller in diameter than said boss to form a snug fit therewith, said means for removably attaching said valve comprising a ring which is threaded to said neck portion, said ring having an interior shoulder on which said outboard side of said valve mount seats, said flexible base of said valve member forming a sealing gasket between said valve mount and a lip on said neck portion defining said container opening.

9. In a breastfeeding assistance device for delivering a liquid diet supplement from a bottle to a nursing infant by way of an elongated flexible tube having a first end communicating with the liquid supplement in the container and a second end which is positioned adjacent a breast nipple for suckling simultaneously with the breast nipple, the improvement comprising:

an outwardly extending collar formed on a member carried on the neck of the bottle, said collar having a plurality of notches formed therein within which said tubing can be wedged and pinched closed when not in use.

10. A method for assisting breastfeeding by delivering a liquid diet supplement to a nursing infant simultaneously with feeding at the breast, comprising the steps of:

providing a non-collapsible container for holding the liquid supplement, said container having a neck portion defining a container opening which is downwardly directed during breastfeeding, said container being otherwise closed, said container including a fluid delivery mechanism comprising a valve mount having a first aperture formed therein through which the interior of said container is accessed for liquid supplement outflow, and a second aperture formed therethrough, a flexible valve member received on said valve mount and covering said second aperture, said valve member being biased to close said second aperture and adapted to substantially prevent liquid supplement from flowing out of said container through said aperture while permitting air to enter said container in response to a negative pressure within said container sufficient to overcome said valve member bias caused by liquid supplement outflow from suckling, said bias being related to a desired level of suckling effort, at least two elongated tubes, one for each breast nipple, carried by said mechanism, each tube having a first end communicating through said opening via said first aperture with said liquid supplement in said container interior, and a second end which is positioned adjacent a breast nipple for suckling, said second end being sized to fit into the infant's mouth simultaneously with the breast nipple, and means for removably attaching said fluid delivery mechanism to said neck portion and sealing said opening;

positioning said device on the user's chest so that said fluid delivery mechanism is at a level in a range from about the same height as a horizontal between the user's breast nipples to slightly below said horizontal to thereby substantially eliminate gravity feed from said container; and locating a tube adjacent a respective breast nipple to enable rapid changeover from one breast to another during feeding.

11. The breastfeeding assistance method of claim 10 wherein said tubing lies against the user's flesh for a portion of its length so that the supplement is warmed by body heat as it passes through said tubing.

12. A device for delivering a liquid diet supplement to a nursing infant simultaneously with normal breastfeeding, comprising:

a non-collapsible container for holding the liquid supplement, said container having a neck portion defining a container opening which is downwardly directed during breastfeeding, said container being otherwise closed;

a fluid delivery mechanism comprising, a valve mount having a first aperture formed therein through which the interior of said container is accessed for liquid supplement outflow, and a second aperture formed therethrough, a plurality of valve members mountable on said valve mount and each having elongated tubing which provides a different rate of delivery for each valve member for a given suckling effort, said plurality of valve members being interchangeable on said valve mount to thereby permit control of liquid supplement delivery by selection of a valve member with the appropriate delivery rate, each said valve member being biased to close said second aperture and adapted to substantially prevent liquid supplement from flowing out of said container through said aperture while permitting air to enter said container in response to a negative pressure within said container sufficient to overcome said valve member bias caused by liquid supplement outflow from suckling, said bias being related to a desired level of suckling effort, said tubing further having a first end communicating through said opening via said first aperture with said liquid supplement in said container interior, and a second end which is positioned adjacent a breast nipple for suckling, said second end being sized to fit into the infant's mouth simultaneously with the breast nipple; and means for removably attaching said fluid delivery mechanism to said neck portion and sealing said opening.

* * * * *

UNITED STATES PATENT AND TRADEMARK OFFICE
CERTIFICATE OF CORRECTION

PATENT NO. : 4,687,466
DATED : August 18, 1987
INVENTOR(S) : Karl O.A.H. Larsson It is certified that error appears in the above-identified patent and that said Letters Patent is hereby corrected as shown below:

Title Page:

IN THE ABSTRACT

In lines 6-7, please delete "communication" and substitute therefor --communicating--;

In the last line of the Abstract, please delete "cloes" and substitute therefor --closed--.

IN THE SUMMARY OF THE INVENTION

In column 2, line 36, please delete "preferable" and substitute therefor --preferably--;

In column 2, line 38, please delete "The position" and substitute therefor --This position--.

IN THE DETAILED DESCRIPTION OF A PRESENTLY PREFERRED EMBODIMENT OF THE INVENTION

In column 3, line 28, please delete "place" and substitute therefor --placed--;

In column 3, line 46, please delete "form" and substitute therefor --from--;

UNITED STATES PATENT AND TRADEMARK OFFICE

CERTIFICATE OF CORRECTION

PATENT NO. : 4,687,466

DATED : August 18, 1987

INVENTOR(S) : Karl O.A.H. Larsson

It is certified that error appears in the above-identified patent and that said Letters Patent is hereby corrected as shown below:

In column 3, line 60, please delete "disk shaped" and substitute therefor --disk-shaped--.

IN THE CLAIMS

In Claim 2 (column 6, line 14), please delete "diskshaped" and substitute therefor --disk-shaped--;

In Claim 5 (column 7, line 2), please delete "removeably" and substitute therefor --removably--.

Signed and Sealed this

Twelfth Day of July, 1988

*Attest:*

DONALD J. QUIGG

*Attesting Officer*

*Commissioner of Patents and Trademarks*